United States Patent
Grandis et al.

(10) Patent No.: US 7,960,360 B2
(45) Date of Patent: Jun. 14, 2011

(54) ANTISENSE GUANIDINIUM PEPTIDE NUCLEIC ACID (GPNA) OLIGONUCLEOTIDES AS ANTITUMOR AGENTS

(76) Inventors: Jennifer Rubin Grandis, Pittsburgh, PA (US); Sufi Mary Thomas, Cheswick, PA (US); Danith H. Ly, Pittsburgh, PA (US)

( * ) Notice: Subject to any disclaimer, the term of this patent is extended or adjusted under 35 U.S.C. 154(b) by 0 days.

(21) Appl. No.: 11/939,018

(22) Filed: Nov. 13, 2007

(65) Prior Publication Data

US 2008/0234181 A1    Sep. 25, 2008

Related U.S. Application Data

(60) Provisional application No. 60/858,571, filed on Nov. 13, 2006.

(51) Int. Cl.
   *A01N 43/04* (2006.01)
   *A61K 31/70* (2006.01)
(52) U.S. Cl. ........................................................ 514/44
(58) Field of Classification Search .................... 514/44
   See application file for complete search history.

(56) References Cited

U.S. PATENT DOCUMENTS

| | | |
|---|---|---|
| 6,187,585 B1 | 2/2001 | Bennett et al. |
| 2002/0155989 A1 | 10/2002 | Efimov et al. |
| 2005/0107325 A1* | 5/2005 | Manoharan et al. ............ 514/44 |
| 2007/0072802 A1 | 3/2007 | Zhao et al. |

OTHER PUBLICATIONS

Escude et al. (Top. Curr. Chem 253:109-148, 2005).*
Zhou et al. (J. Am. Chem. Soc. 125:6878-6879, 2003).*
Dragulescu-Andrasi et al., "Cell-permeable GPNA with appropriate backbone stereochemistry . . . ," Chem. Commun., 2005, pp. 244-246.
Wender, P. et al., "The design, synthesis, and evaluation of molecules . . . " PNAS, vol. 97, No. 24, pp. 13003-13008, Nov. 21, 2000.

* cited by examiner

*Primary Examiner* — Brian Whiteman
(74) *Attorney, Agent, or Firm* — Barbara E. Johnson, Esq.

(57) ABSTRACT

A class of antisense agents having a distributed guanidinium peptide nucleic acids (GPNA) backbone which has excellent uptake into mammalian cells, can bind to the target DNA or RNA in a highly sequence specific manner and can resist nucleases and proteases both outside and inside the cell(s) of interest. In one embodiment, either systemic or intratumoral administration of antisense Epidermal Growth Factor Receptor ("EGFR") GPNA oligonucleotides is believed to down-modulate EGFR levels, thus in turn to reduce head and neck squamous cell carcinoma tumor growth, which has been confirmed to date both in vitro and in vivo.

1 Claim, 2 Drawing Sheets

US 7,960,360 B2

SEQUENCE LISTING

```
<160> NUMBER OF SEQ ID NOS: 10

<210> SEQ ID NO 1
<211> LENGTH: 16
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 1
agcagctccc attggg                                                     16

<210> SEQ ID NO 2
<211> LENGTH: 22
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 2
tcggggagca gcgargcgac cc                                              22

<210> SEQ ID NO 3
<211> LENGTH: 16
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 3
ggtcgcatcg ctgctc                                                     16

<210> SEQ ID NO 4
<211> LENGTH: 13
<212> TYPE: DNA
<213> ORGANISM: Artificial
<220> FEATURE:
<223> OTHER INFORMATION: guanidinium peptide nucleic acid EGFRAS
      sequence targeting 5' end
```

```
<400> SEQUENCE: 4
cgcatcgctg ctc                                              13

<210> SEQ ID NO 5
<211> LENGTH: 14
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 5
gtcgcatcgc rgct                                             14

<210> SEQ ID NO 6
<211> LENGTH: 16
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 6
gcatcgctgc tccccg                                           16

<210> SEQ ID NO 7
<211> LENGTH: 16
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 7
agcagctccc attggg                                           16

<210> SEQ ID NO 8
<211> LENGTH: 18
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 8
cctccgtggt cargctcc                                         18

<210> SEQ ID NO 9
<211> LENGTH: 20
<212> TYPE: DNA
<213> ORGANISM: Artificial
<220> FEATURE:
<223> OTHER INFORMATION: guanidinium peptide nucleic acid EGFRAS
      sequence targeting 5' end

<400> SEQUENCE: 9
ccccagcagc tcccattggg                                       20

<210> SEQ ID NO 10
<211> LENGTH: 18
<212> TYPE: DNA
```

-continued

```
<213> ORGANISM: Artificial
<220> FEATURE:
<223> OTHER INFORMATION: guanidinium peptide nucleic acid EGFRAS
      sequence targeting 5' end

<400> SEQUENCE: 10
cggagggtcg catcgctg                                              18
```

ANTISENSE GUANIDINIUM PEPTIDE NUCLEIC ACID (GPNA) OLIGONUCLEOTIDES AS ANTITUMOR AGENTS

CROSS REFERENCE TO RELATED APPLICATIONS

This application claims priority to U.S. Provisional Patent Application No. 60/858,571 filed Nov. 13, 2006, which is herein incorporated by reference in its entirety.

BACKGROUND OF THE INVENTION

1. Field of the Invention

The invention pertains to GPNA oligonucleotides, and in particular to EGFRAS GPNA oligonucleotides, which has utility in treating malignant tumors.

2. Description of Related Art

Among other cancers, head and neck squamous cell carcinoma (HNSCC) is an aggressive malignancy that is difficult to treat with conventional therapies. Despite significant advances over the past 3 decades, current treatment modalities including surgery, radio- and chemotherapy have not improved five-year survival rates in HNSCC patients. Molecular signatures of HNSCC—indeed, all—malignancies is a topic of great current interest.

The Epidermal Growth Factor Receptor (EGFR) has emerged as a promising molecular target in the past decade or so, and in particular EGFR is upregulated in the majority of HNSCC tumors, so it is not surprising that preclinical model inhibition of EGFR has resulted in tumor inhibition. Notably, increased EGFR levels in HNSCC tumors have been associated with advanced stage, large tumor size, invasion, decreased survival and poor prognosis. Notwithstanding this preclinical promise, clinical trials using agents that inhibit EGFR activation and signaling have demonstrated limited antitumor efficacy. Another popular approach to target EGFR is to downmodulate its expression levels. Antisense DNA sequences that bind target DNA or mRNA inhibiting transcription or translation are highly effective in inhibiting HNSCC. However, DNA based agents are prone to nuclease degradation and hence have short half-lives in plasma, and RNA- and/or DNA-based antisense agents are not cell-permeable, necessitating the finding of a carrier or effective modification before the agent can pass the cell membrane. Heretofore, then, the dual or triple goals of enzymatic stability, cell-permeability and antitumor effects have not been achieved by methods and agents known prior to the present invention.

Therefore, a need remains for a way to administer antisense agents such as EGFR Antisense (EGFRAS)—whether as complete genes or as oligonucleotides—that are resistant to nucleases and proteases and thus can be given to patients systemically, i.e., parenterally or via other appropriate systemic administration, to combat HNSCC and other malignancies for which such treatment is indicated.

SUMMARY OF THE INVENTION

In order to meet this need, the present invention is a class of antisense agents having a guanidinium peptide nucleic acid (GPNA) backbone which has excellent uptake into mammalian cells, can bind to the target DNA or RNA in a highly sequence specific manner and can resist nucleases and proteases both outside and inside the cell(s) of interest. In particular, either systemic or intratumoral administration of EGFRAS-GPNA oligonucleotides is believed to downmodulate EGFR levels, thus in turn to reduce HNSCC tumor growth, and this has been confirmed to date both in vitro and in vivo. Systemic administration of the particular improved antisense oligonucleotides of the present invention has already exhibited antitumor activity.

BRIEF DESCRIPTION OF THE DRAWING(S)

DESCRIPTION OF THE PREFERRED EMBODIMENT(S)

Figure 1:
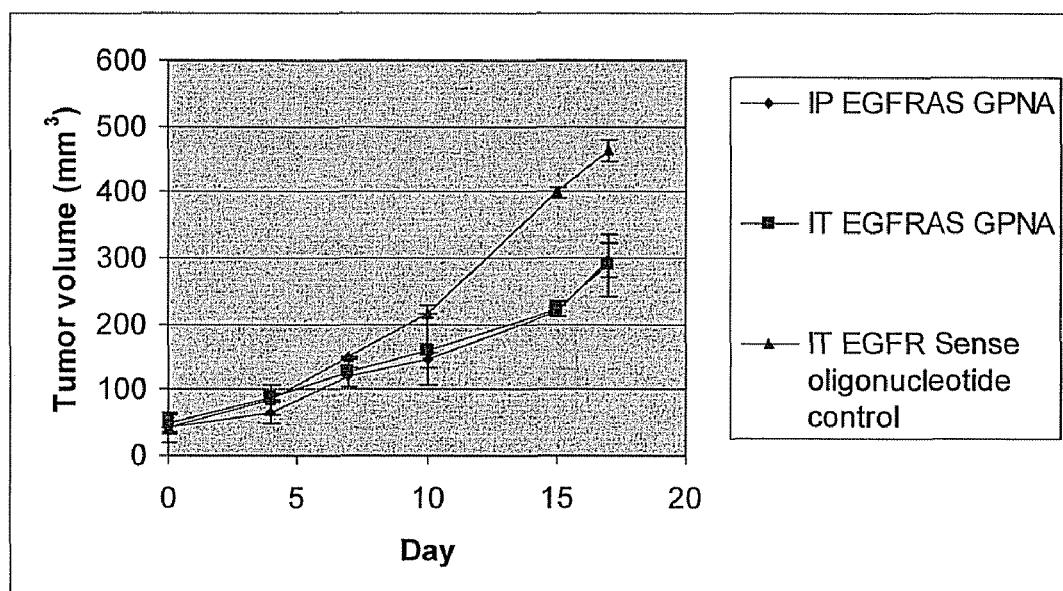
FIG. 1 is a line graph contrasting the efficacy of intraperitoneal (IP) injection of EGFRAS GPNA with the intratumoral (IT) administration of both EGFRAS GPNA and EGFR Sense oligonucleotide control, in mice.

The present invention is a class of antisense agents having a peptide backbone, called guanidinium peptide nucleic acids (GPNA), which can bind to the target DNA or RNA in a highly sequence specific manner while evincing resistance to nucleases and proteases. In particular, either systemic or intratumoral administration of EGFRAS-GPNA oligonucleotides is believed to downmodulate EGFR levels, thus in turn to reduce HNSCC tumor growth, and this has been confirmed to date both in vitro and in vivo.

The present invention realizes the power of PNAs and PTDs, defined and explained below, in a new and particular way. Peptide Nucleic Acids (PNAs) were known—prior to the present invention—for use as moieties in association with oligonucleotides in order to make the oligonucleotides more stable. Not only were PNAs already known to impart this stabilization to oligonucleotides—PNAs were believed to have been invented in Denmark circa 1991—it was also believed prior to the present invention that particular PNAs could at least theoretically be used to improve the uptake of PNAs into the cells (i.e., tissues such as tumor tissues) of interest. For example, it was believed that by adding a Protein Transduction Domain (PTD) to a PNA, the oligonucleotide-PNA-PTD combination would have increased uptake into cells. Previously known PTDs included one or more arginine residues with a guanidinium portion that rendered the resultant molecule amphipathic and concomitantly more able to pass through cell membranes than non-amphipathic molecules. Unfortunately, these known PTDs were also unacceptably toxic to cells, as a general proposition. Therefore, as a part of the present invention the PTD of the PNA of the present oligonucleotides is positioned such that the PTD is protected by the PNA—by positioning the PTD within the PNA. This positioning of the PTD within the PNA increased the melting point of the PNA/PTD/oligonucleotides to as high as 80° C. and increased the lipophilicity of the PNA/PTD/ oligonucleotides such that not only did almost 100% of the oligonucleotides enter the cells without the need for an additional carrier, such as a liposome, but the cell viability remained nearly 100% as well. The present invention, then, is generally any oligonucleotide derivative having a PTD located within the associated PNA (see the below descriptions of distributed and/or alternating guanidinium residues), and specifically the present invention embraces at least one particular EGFRAS GPNA oligonucleotide believed to cause new and unexpected therapeutic results when administered—particularly to patients having HNSCC tumors—either intratumorally or, almost unbelievably, systemically.

Those skilled in the art know, at this writing, that EGFR inhibition may be achieved by either blocking EGFR autophosphorylation or by downmodulating total EGFR levels within the cells of interest. Monoclonal antibodies and tyrosine kinase inhibitors that block EGFR have demonstrated limited antitumor effects in clinical trials, unfortunately. This limited efficacy may be due to several reasons including but not limited to rapid receptor turnover and inefficient blockade of the overexpressed receptor. Receptor downmodulation may circumvent the problem of inefficient receptor inactivation. Previous reports demonstrate that EGFR antisense gene therapy can effectively downmodulate EGFR expression reducing HNSCC tumor cell viability. Preliminary results of a Phase I clinical trial in HNSCC patients indicate a ~430% clinical response rate with intratumoral delivery of an EGFR antisense gene. Although gene therapy cannot be delivered systemically, antisense oligonucleotides have proven feasible in cancer patients when the oligonucleotides are administered intratumorally. The administration of antisense oligonucleotides has been limited, in the prior art, to intratumoral administration at least in part because prior art antisense oligonucleotides are rapidly degraded by serum nucleases and because traditional PNAs having PTDs were too toxic to use.

The present GPNA oligonucleotides contain in part PNAs which, in detail, are DNA analogues in which the sugar-phosphate backbone is replaced by a pseudopeptide chain of N-(2-aminoethyl) glycine monomers covalently bonded to DNA bases. Nonionic PNAs form highly stable duplexes (through Watson-Crick base-pairing to form a hybrid) with complementary DNA and RNA strands and thus inhibit replication, transcription and translation of the template. The ability of PNAs to resist proteases and nucleases, and to hybridize stably, make PNAs attractive tools for biotechnology applications. Unfortunately, despite their neutral charge on the backbone, PNAs are not readily taken up by mammalian cells and, as described above, known PNAs with PTDs have been recognized as too toxic for therapeutic use, so without improvements in PNAs their adoption has been and would have continued to be extremely limited. In this context, then, the inclusion of the below-described internally linked D-arginine side chains is critical to the invention, and preferably the guanidine residues are distributed (and more preferably alternatively distributed with unmodified PNAs) throughout the oligonucleotide of interest.

The GPNAs of the present invention contain internally-linked D-arginine side chains (guanidinium residues) and bind to RNA with high affinity and sequence selectivity—and are readily taken up by mammalian cells. The present GPNAs, particularly the EGFRAS GPNAs, are believed to bind to the transcriptional start site of the EGFR gene to induce potent and sequence-specific antisense effects, in a manner less toxic than with a more traditional PNA-polyarginine conjugate.

In a manner typical of other syntheses according to the invention, GPNA monomers have been synthesized according to an established solid-phase Boc chemistry protocol. EGFRAS GPNA oligomers were synthesized in three steps: 1) removal of the Boc-protecting group from the terminal amine; 2) coupling of the next GPNA monomer onto the N-terminus of the growing chain and 3) capping of the unreacted amines with acetic anhydride. Following the complete coupling of the last monomer, GPNA were cleaved from the resins and the protecting groups were removed from the nucleobases and the guanidine group. The crude products were precipitated with ethyl ether and purified by reverse-phase HPLC. The resulting EGFRAS GPNA were resuspended in water and characterized by MALDI-TOF mass spectrometry. In order to determine the efficiency of uptake of the GPNA in HNSCC cells, fluorescently tagged EGFRAS GPNA was also synthesized, namely, a 16-base GPNA spanning nucleotides 764-779 on the EGFR mRNA. On binding to its target, the C terminus of the GPNA $A_RGC_RAG_RCT_RCC_RCA_RTT_RGG_RG$ (SEQ ID NO:1) binds to the 5' end of the mRNA or DNA targeted within the cell(s) to be treated. Alternative sequences could be, without limitation, those which target the transcriptional start site, such as, $T_RCG_RGG_RGA_RGC_RAG_RCG_RAT_RGC_RGA_RCC_RC$;     (SEQ ID NO: 2)

or those which target the translational start site, such as $G_RGT_RCG_RCA_RTC_RGC_RTG_RCT_RC$,     (SEQ ID NO: 3)

$C_RGC_RAT_RCG_RCT_RGC_RTC$,     (SEQ ID NO: 4)

$G_RTC_RGC_RAT_RCG_RCT_RGC_RT$,     (SEQ ID NO: 5)

$G_RCA_RTC_RGC_RTG_RCT_RCC_RCC_RG$;     (SEQ ID NO: 6)

or additional alternative sequences including but not limited to $AG_RCA_RGC_RTC_RCC_RAT_RTG_RGG$,     (SEQ ID NO: 7)

$C_RCT_RCC_RGT_RGG_RTC_RAT_RGC_RTC_RC$,     (SEQ ID NO: 8)

$C_RCC_RCA_RGC_RAG_RCT_RCC_RCA_RTT_RGG_RG$,     (SEQ ID NO: 9)

$C_RGG_RAG_RGG_RTC_RGC_RAT_RCG_RCT_RG$.     (SEQ ID NO: 10)

The R groups indicate the guanidinium substituents, namely, N-(2-aminoethyl)D-arginine. In theory, although applicants do not intend to be bound by the theory, the distribution of the guanidinium residues throughout the oligonucleotide creates a conformational effect which contributes to lower toxicity of the oligonucleotide than when guanidinium groups are provided to oligonucleotides in a less evenly distributed fashion. It should be noted in the above GPNA sequences that each nucleotide base without R residues are substituted with unmodified PNA, namely, N-(2-aminoethyl) glycine, such that the present GPNAs are indeed true PNAs even though every nucleotide base is not guanidinium-substituted. In the preferred embodiment of the present invention, the unmodified PNA and arginine-derived GPNA substitutions alternate at every other nucleotide base position. However, alternate embodiments of the invention embrace both greater and lesser guanidinium-substitution, namely, at every nucleotide base position, at every third, fourth or fifth nucleotide base substitution or any regular or irregular pattern of guanidinium substitution in the ratio of from 1:1 nucleotide base:guanidinium group to 5:1 nucleotide base:guanidinium group, because as few as four guanidinium groups per oligomer can enhance uptake into the cells in contrast to oligomers having no guanidinium substitution.

The invention is described with special particularity in the following Examples.

EXAMPLE 1

In vivo antitumor efficacy of EGFR antisense GPNA: As shown in FIG. 1, in order to examine the antitumor efficacy of EGFRAS GPNA ($A_RGC_RAG_RCT_RCC_RCA_RTT_RGG_RG$ (SEQ ID NO: 1)) in vivo a preliminary study was carried out in which athymic nude mice were inoculated with head and neck squamous cell carcinoma (HNSCC) cell line 1483 ($10^6$ cells per site). Tumors were allowed to establish for 10 days. The tumor volumes were measured using a vernier caliper. Mice were randomized into three groups such that the average of the tumor volumes in each group was the same. Two mice were treated with intraperitoneal (IP) injections of EGFRAS GPNA. Three mice were treated with intratumoral (IT) injections of EGFRAS GPNA and two mice were treated with EGFR sense oligonucleotide as a control. The mice were injected once per day for six days per week. Mice were administered 50 micrograms EGFRAS GPNA or EGFR sense oligonucleotide IT and 100 micrograms EGFRAS GPNA IP. Treatment was carried out for 16 days. Tumors were measured twice a week in 2 dimensions using a vernier caliper. Tumor volumes were estimated using the formula length×width (smaller dimension)/2. The results of the study were as follows. Mice treated with EGFRAS GPNA IT or IP had smaller tumors compared to the control EGFR sense oligonucleotides treated mice. There was no significant difference between tumor volumes of IT and IP treated EGFRAS GPNA groups, indicating that IP administration of GPNA is a feasible route of delivery. There was no apparently toxicity observed due to EGFRAS GPNA treatment.

EXAMPLE 2

Figure 2:
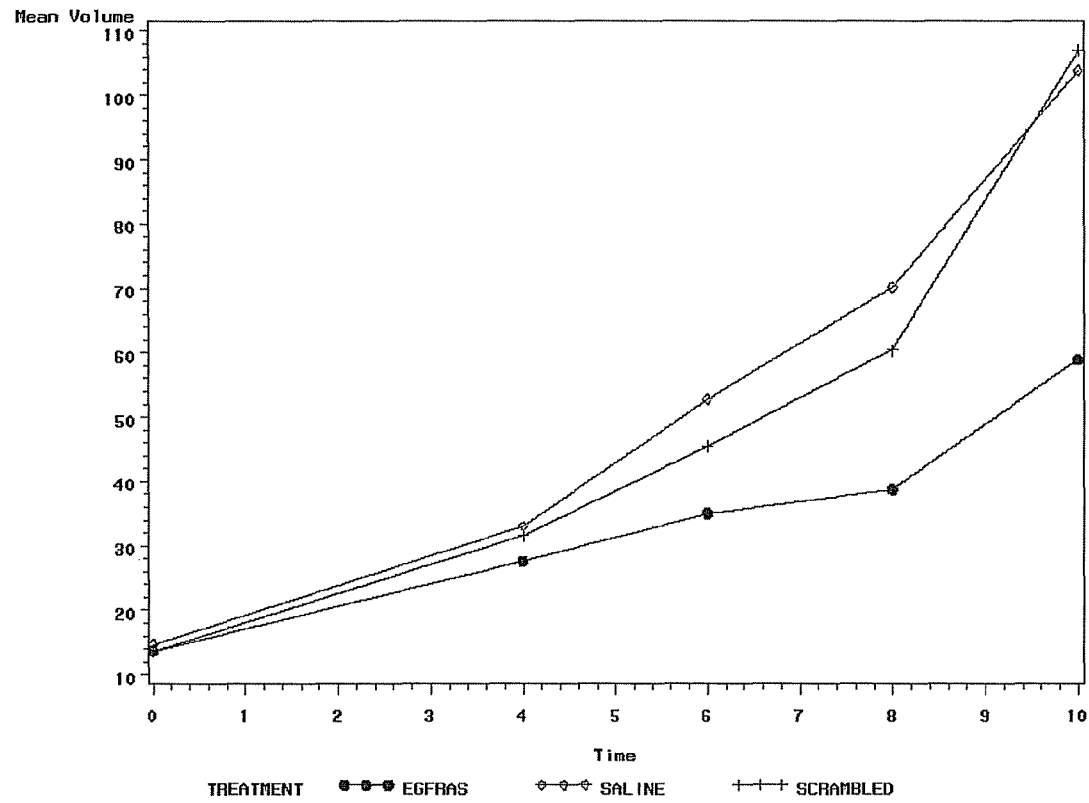
FIG. 2 is a line graph contrasting systemic delivery of EGFRAS GPNA and EGFR "scrambled;" in mice.

Systemic delivery of EGFRAS GPNA has specific antitumor effects in HNSCC xenografts: Referring now to FIG. 2, athymic nude mice were inoculated with HNSCC cell line 1483 subcutaneously with one million cells per flank. Animals were randomized into 3 groups based up on the tumor volumes. There were 11 mice in the EGFRAS GPNA group and 10 mice each in the saline and the EGFR scrambled groups. Saline or GPNA (5 mg/kg body weight) were administered via IP injections 5 days a week. Treatment was carried out for 10 days. Tumors were measured twice a week in 2 dimensions using a vernier caliper. Tumor volumes were estimated using the formula length×width (smaller dimension)/2. There was a significant difference in the tumor volumes of mice treated with EGFR antisense GPNA compared to the scrambled GPNA ($P<0.01$). There was no significant difference between the tumor volumes of mice treated with the scrambled GPNA and saline.

The invention claimed is:

1. A method for the treatment of malignancy comprising administering systemically or intratumorally an oligonucleotide comprising at least one peptide nucleic acid "PNA," the peptide nucleic acid comprising a guanidinium peptide (GPNA), to a patient in need of such treatment, further wherein said oligonucleotide consists of a 16-base GPNA spanning nucleotides 764-779 on an EGFR mRNA wherein said molecule contains GPNA substitutions at every other nucleotide.

* * * * *